United States Patent [19]

Dugge

[11] Patent Number: 4,867,073
[45] Date of Patent: Sep. 19, 1989

[54] INTERNAL DRAINAGE SYSTEM FOR HOLLOW MEMBER STRUCTURAL ASSEMBLY AND METHOD

[75] Inventor: Richard H. Dugge, Des Peres, Mo.

[73] Assignee: ACF Industries, Inc., Earth City, Mo.

[21] Appl. No.: 169,458

[22] Filed: Mar. 17, 1988

[51] Int. Cl.[4] .............................................. B61D 7/02
[52] U.S. Cl. ..................................... 105/358; 105/407
[58] Field of Search ............... 105/247, 248, 358, 359, 105/404, 411, 407, 409, 377, 463.1, 360; 296/208, 154, 213; 52/302; 280/782

[56] References Cited

U.S. PATENT DOCUMENTS

| 2,033,750 | 3/1936 | Westrope | 296/154 X |
| 2,821,429 | 1/1958 | Rantala | 296/208 |
| 3,768,422 | 10/1973 | Shaver et al. | 105/409 |
| 3,830,167 | 8/1974 | Tamborski et al. | 105/409 X |
| 4,101,175 | 7/1978 | Kull | 105/248 X |
| 4,230,048 | 10/1980 | Gordon et al. | 105/358 X |
| 4,377,058 | 3/1983 | Hallam et al. | 105/377 X |
| 4,445,721 | 5/1984 | Yaotani et al. | 296/154 |
| 4,582,358 | 4/1986 | Draper | 296/213 |

Primary Examiner—Johnny D. Cherry
Assistant Examiner—Joseph D. Pape
Attorney, Agent, or Firm—Polster, Polster and Lucchesi

[57] ABSTRACT

An internal water drainage system for an interconnected hollow structural assembly within a railroad pressure discharge hopper car or the like is disclosed. To facilitate water drainage throughout the interconnected hollow structural assembly following hydrostatic pressure testing of the car, water draining passageways are provided in the hollow structural members in an area of juncture between the members, at least along a lowermost extent of each of the hollow structural members. The water drainage passageways are constructed to communicate with a water drain opening provided in the shell of the railroad car, in order to afford gravity flow of water through the hollow structural members and evacuation from the railroad car. A method for hydrostatic pressure testing of a railroad car is also disclosed in which gravity flow evacuation of water through the hollow structural members is achieved by utilizing gravity flow of water throughout. In both the aforementioned assembly and method, water deterioration, corrosion, and the like after hydrostatic pressure testing are substantially minimized or totally eliminated.

10 Claims, 2 Drawing Sheets

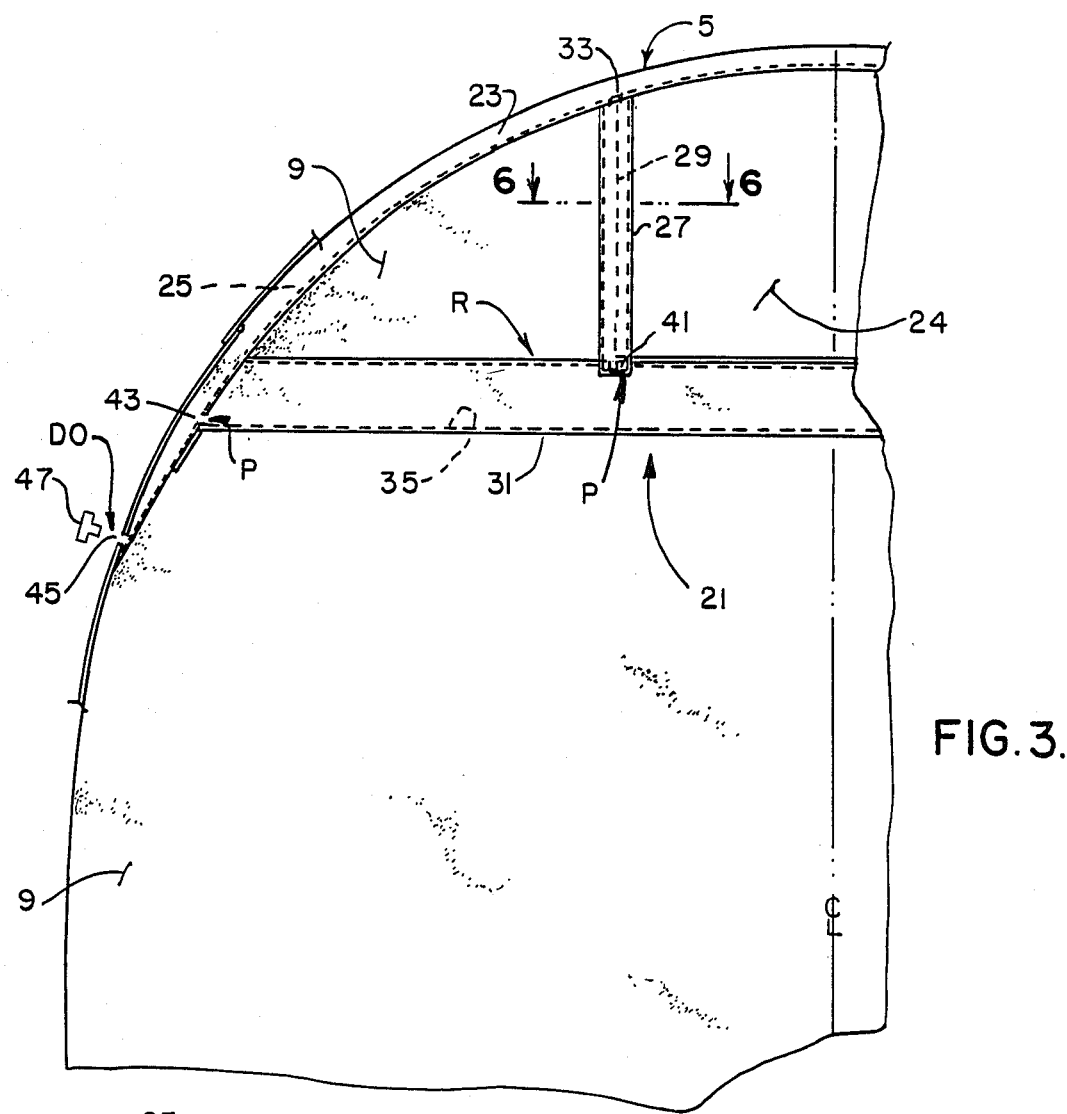
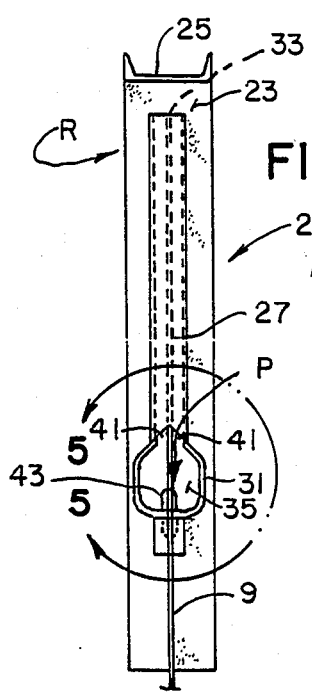
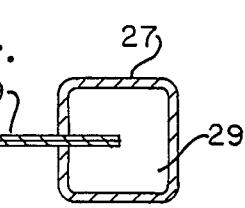
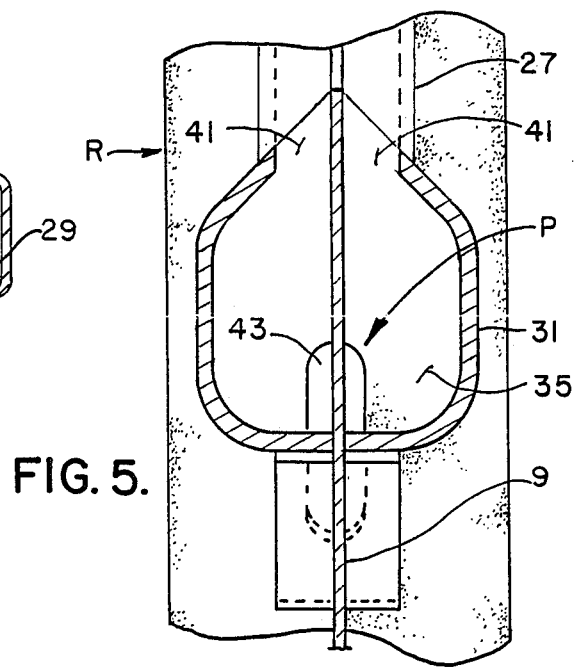

INTERNAL DRAINAGE SYSTEM FOR HOLLOW MEMBER STRUCTURAL ASSEMBLY AND METHOD

BACKGROUND OF THE INVENTION

This invention relates to internal water drainage of a hollow member structural assembly in a railroad pressure discharge hopper car or the like, including a method for drainage of the hollow member structural assembly after hydrostatic testing of the railroad car.

Powdered, bulk commodities (i.e., flour, starch and talc) as oftentimes transported in pressure differential covered hopper cars. These cars are constructed to accommodate a predetermined internal pressure in order to allow pressure discharge unloading of the bulk commodity from within the railroad car. Fast and efficient unloading of the commodity to remote receiving bins of a customer is thus possible. For example, unloading rates of up to 100,000 pounds per hour may be achieved where the internal pressure of the car is operated at about 14.5 psi. This means that the hopper car must accommodate that amount of internal pressure (with an adequate safety factor) during unloading without causing damage to any of the structural components of the car.

In order to verify the structural integrity of each such pressure discharge rail car manufactured, each such car is subjected a predetermined internal pressure. For such testing, hydrostatic pressure testing is used, following construction of the car. This method requires the hopper car to be filled with water and then to be pressurized to a predetermined pressure in order to verify the structural integrity of the railroad hopper car and its structural components.

In some cases, such pressure discharge hopper cars are provided with a number of adjacent hoppers or compartments which are separated by compartment partition walls or bulkheads. These partition walls or bulkheads terminate short of the top or upper end of the hopper car in order to permit the powdered bulk commodities to fill up each compartment and then flow into an adjacent compartment through large openings between the top of the compartment walls or bulkheads and the top of the hopper car. Typically, interconnected hollow structural members are provided for internally supporting and reinforcing the compartment walls or the bulkheads relative to the elongated shell which forms the hopper car.

Since these hollow structural members may not be airtight during pressure testing of the car, these hollow structural members oftentimes become filled with water during the hydrostatic pressure testing of the hopper car. While the water used in hydrostatic testing each of the railcars manufactured can be easily removed through bottom outlets associated with each compartment or hopper, it has been found that some residual water remains trapped in the interconnected hollow structural members. Unfortunately, this results in water deterioration and corrosion of the internal surfaces along the compartment walls or bulkheads and other internal surfaces within the compartments or hoppers. Also over time, this entrapped water, often having a high concentration of rust, seeps out of the hollow members and discolors the interior of the car and the lining and may partially contaminate a lading. Because customers demand purity in the powdered bulk commodities, any rust from the inside of the compartments, caused by water deterioration, can create substantial problems. Therefore, when residual water remains inside the interconnected hollow structural members and causes damage to inside surfaces of the hopper car, it is necessary to rework such surfaces and remove all corrosion and other debris. This often means that the lining for the car must be repaired. As can be appreciated, this is not only costly, but is a time consuming process requiring inspection and subsequent repair of any deteriorated surfaces in the hopper car.

SUMMARY OF THE INVENTION

Among the several objects and features of this invention may be noted:

The provision of an internal water drainage system for an interconnected hollow structural assembly within a railroad hopper car or the like, in which the interconnected hollow structural assembly is constructed to provide internal water drainage therethrough for the ready evacuation of the water after hydrostatic testing and before lining the car;

The provision of such an internal water drainage system which provides gravity flow evacuation of water from the hollow structural assembly;

The provision of such an internal water drainage system which substantially minimizes and/or eliminates any subsequent water deterioration problems, as well as the time and expense of repairing such problems; and The provision of such an internal water drainage system which retains the structural integrity of the hollow structural assembly while affording water drainage throughout the assembly, which effectively utilizes gravity in removing water throughout the assembly, which is really incorporated in the design of such a railway car without substantial additional cost, which results in substantial labor savings during fabrication and lining of such a railway car, and which provides substantial economic savings by not requiring any subsequent repairing or resurfacing of the internal surfaces of the hopper car.

Briefly stated, an internal water drainage system of the present invention for a hollow structural assembly may be used in a railroad car (or other such structure) having a shell. The hollow structural assembly includes interconnected hollow structural members for internal support of the shell or other structural members. At least one of the hollow structural members is positioned at least partially below another hollow structural member. A water draining passageway is formed in such hollow structural members in an area of juncture between the members, and a water drain opening is formed in the shell which communicates and cooperates with the water drainage passageway provided in the hollow structural members in order to facilitate gravity flow of water through the hollow structural members for evacuation and removal from the shell via the drain opening. In addition to the aforesaid internal water drainage hollow structural assembly, a method for hydrostatic pressure testing of a railroad car is disclosed which employs gravity flow evacuation of water from the shell of a railroad car including interconnected hollow structural members therein, by utilizing gravity flow removal of water throughout for evacuation from the tank car. Following removal of the water from the railroad car including the associated interconnected hollow structural members, the water draining openings in the tank car are sealed off.

Other objects and features of this invention will become apparent from the ensuing description.

BRIEF DESCRIPTION OF THE DRAWINGS

FIG. 3 is a fragmentary end cross sectional view, taken along lines 3—3 of FIG. 2, illustrating the internal drainage system of the present invention for a hollow structural assembly of the present invention;

FIG. 4 is a side elevational view of the hollow structural assembly shown in FIG. 3 including the internal water drainage system of the present invention;

FIG. 5 is an enlarged fragmentary view taken on line 5—5 of FIG. 4, partially in section, of a horizontally extending hollow structural member of the aforesaid hollow structural assembly including water drainage passageways associated therewith in accordance with the present invention; and FIG. 6 is an enlarged fragmentary sectional view taken along line 6—6 of FIG. 3 of a vertically extending hollow structural member constituting a portion of the aforesaid hollow structural assembly.

DESCRIPTION OF THE PREFERRED EMBODIMENT

Figure 1:
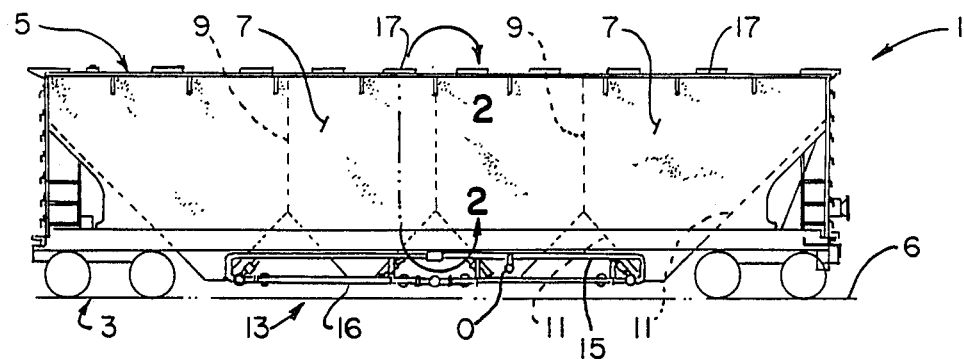
FIG. 1 is a side elevational view of a railroad hopper car in which an internal water drainage system of the present invention is incorporated in a hollow structural assembly.
Figure 2:
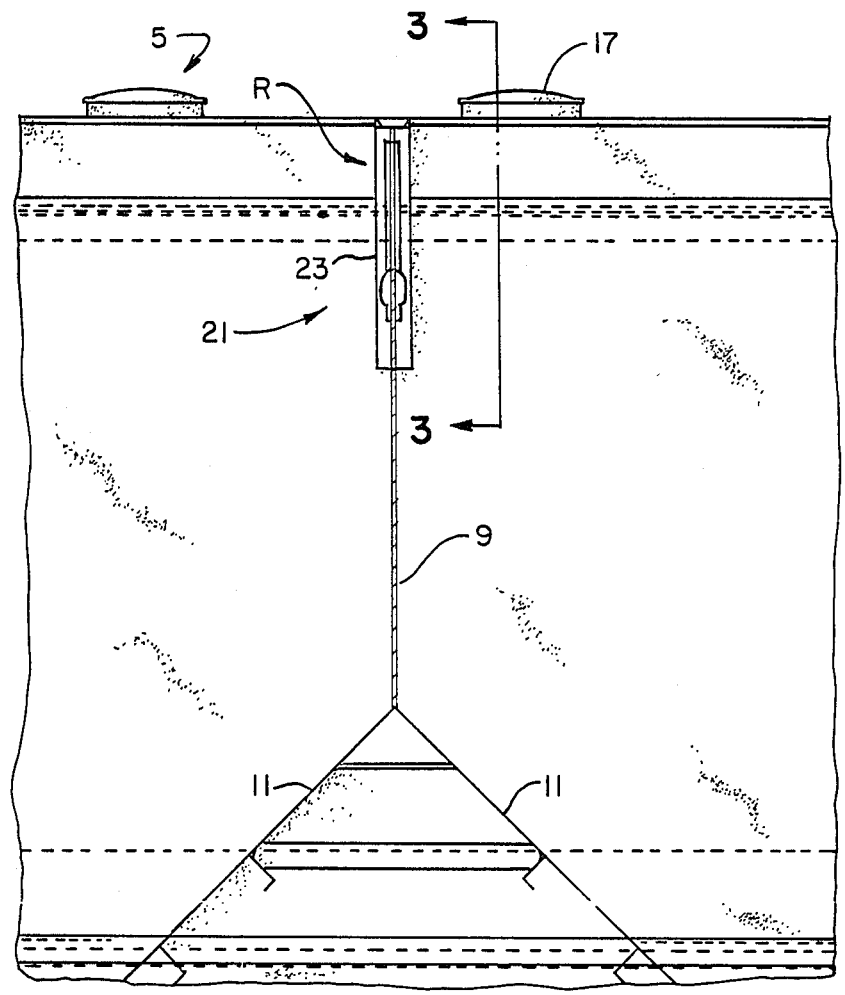
FIG. 2 is a fragmentary side cross sectional view taken along line 2—2 of FIG. 1 on an enlarged scale illustrating the use of interconnected hollow structural members in the upper end of a compartment partition wall or bulkhead and the roof of a railroad hopper car.

A pressure differential railroad hopper car 1, as shown in FIG. 1 of the drawings, is designed to handle powdered or other dry, fluent bulk commodities, such as flour, starch, talc and the like. Car 1 includes an undercarriage wheel structure 3 which rollingly supports an elongated and unitary car body or shell 5 on rails 6. Within the shell 5, there are a plurality of compartments or hoppers 7 which are separated from one another by generally vertically directed compartment partition walls or bulkheads 9. In FIG. 1, the bulkheads 9 are shown in broken lines and are connected at their lower ends to downwardly and inwardly tapering sloping walls or slope sheets 11 which converge toward an outlet opening O for unloading the contents for each hopper 7. Connected to each product discharge outlet opening O is a product discharge system 13 having a pipe or piping 15 connected to each of the hoppers 7 in order to allow internal pressurization of the car. Product discharge system 13 further includes a discharge pipe 16 connected to each outlet O for pneumatically conveying the lading from the car. Loading hatches 17 are provided on the car body roof are for loading a lading into the hoppers 7. When hatches 17 are closed, the lading is maintained in a dry and sanitary condition. Hatches 17 are so constructed as to permit internal pressurization of car body 5.

Unloading rates up to 100,000 pounds per hour may be achieved, depending on the type of commodity, and the length, size and configuration of the conveying lines. In order to achieve fast and efficient unloading from the hopper car 1, it is necessary that hopper car 1 be internally pressurized to a predetermined internal pressure without damage to the car. It has been found that unloading rates of up to 100,000 pounds per hour may be achieved where the car is operated at about 14.5 PSI. Other cars may be operated at lower or higher levels of internal pressurization.

Hydrostatic pressure testing of the hopper car 1, after construction, is the typical method of establishing and verifying the predetermined internal pressure desired for the hopper car 1. The hopper car 1 is filled with water and pressurized to a predetermined level, e.g., 22.5 PSI, to determine the structural integrity of shell 5, as well any other structural components within the railroad car 1 which are subjected to this pressure loading. As will be discussed in detail below, bulkheads 9 may be reinforced, as generally indicated at R, with interconnected hollow structural members (as will appear) at the upper end thereof for reinforcing and supporting the upper portions of bulkheads 9 proximate the roof of hopper car 1.

Following hydrostatic pressure testing of the hopper car 1, the water is drained therefrom. However, since in normal operation, the hollow structural members may not be airtight, during hydrostatic testing, water may seep in to these hollow structural members and become entrapped therewithin. This entrapped water will, in many instances, cause the inner surfaces of the hollow structural members to rust or to otherwise corrode. The entrapped water may thus become laden with rust. If this rusty water leaks from within the hollow members (which it often does), it will stain, damage, or contaminate the inside of the car or the lading. It should also be realized that such testing is performed before painting and lining of the car. Oftentimes, this rusty water will leak out of the hollow members after painting or lining of the car and will be quite visible. This requires substantial reworking of the interior surfaces of the hopper car 1 in order to remove all corrosion and other debris caused by water deterioration, and may require a costly repair of the lining or paint. The present invention is directed toward solving this problem in order to minimize or to substaintially eliminate the need for expensive and time consuming re-working or repair of the interior surfaces of the hopper car 1.

While, within the broad aspects of the present invention, the water drainage system and method of the present invention may be utilized in connection with interconnected hollow structural members used for any purpose, it is particularly useful in the fabrication of railroad cars or the like.

Specifically, and as shown in FIGS. 2-6 of the drawings, the reinforcement system R of the present invention comprises an interconnected hollow structural members assembly 21 which is secured to the upper ends of at least certain of the bulkheads 9 and to the inner face of the car body 5 roof proximate the upper ends of the bulkheads 9. While the shape and orientation of the interconnected hollow structural assembly 21 may be varied to suit the particulars required, in the illustrated and disclosed embodiment, as will presently be described, they preferably include generally vertically extending, generally horizontally extending, and generally curvilinearly extending hollow structural members.

As best seen in FIG. 3 of the drawings, a curvilinear channel-shaped member 23, which has a shape corresponding to the curvature of the roof of shell 5, has its channel opening 25 positioned toward the roof. Since FIG. 3 represents approximately one half of the interconnecting hollow structural member assembly 21, the curvilinear channel shaped member 23 extends equidistantly downwardly from the center line shown in FIG. 3 on opposite side of the shell.

An opening 24 is provided in the upper central margin of partition sheet 9 adjacent the roof. The inner connected hollow structural member assembly 21 further includes a generally vertically oriented, hollow structural member 27 having a square tube configuration, as shown in FIG. 6 of the drawings. The upper end of the hollow structural member 27 is connected to channel member 23, with the channel opening 25 of the channel-shaped member 23 in communication with the interior 29 of the generally vertically oriented hollow structural member 27. Since the FIG. 3 representation illustrates approximately one-half of the interconnected hollow structural member assembly 21, there is preferably provided a corresponding vertically oriented structural members 27 on opposite sides of the center line as shown in FIG. 3.

The lower end of each generally vertically oriented hollow structural member 27 is attached to a generally horizontally extending hollow structural member 31. It is to be noted that the portions of bulkhead 9 defining opening 24 extend through the horizontally extending hollow structural member 31 and the vertically oriented hollow structural member 27. Further, the upper margins of partition sheet 9 abut the downwardly facing closed face of the curvilinear channel-shaped member 23, to provide a structurally integrated support or reinforcement for the bulkhead 9 in conjunction with the upper inner wall of shell 5. The area bounded by the spaced vertically oriented hollow structural members 27, the horizontally extending member 31 and the curvilinear channel-shaped member 23, at the top of each bulkhead 9, defines opening 24 through which a powdered bulk commodity (lading) can be transferred between the hoppers or compartments during the loading process. In this manner two or more hoppers 7 may be simultaneously loaded using a singe hatch 17.

This just described interconnected hollow structural member assembly 21 is typically used in providing internal reinforcing support for bulkheads 9 at the upper ends thereof and for the upper portion of shell 5. Such structure, when subjected to hydrostatic pressure testing, oftentimes allows water to run (leak) into the channel opening 25 of the channel-shaped member 23 and into the interior 29 of the hollow structural members 27 and 31. Following the hydrostatic pressure testing, the water within the hopper car 1 can be removed from the hoppers, by way of the sloping surfaces or sheets 11 through the discharge outlets (not shown). However, some water may remain trapped within the hollow structural member assembly 21 and may not begin to leak from the hollow members for some time after hydrostatic testing.

In accordance with the present invention, appropriately placed water draining passageways P may be are provided in the interconnected hollow structural member assembly 21 for communication with a water drain opening DO (see FIG. 3) provided in shell 5 at an appropriate location for the prompt and substantially complete draining of such entrapped water from within the hollow members of assembly 21. Specifically, it will be seen that the channel opening 25 of the channel-shaped member 23 is in communication with the interior 29, as indicated at 33, of the vertically oriented hollow structural member 27 so that water may readily be drained therefrom after hydrostatic pressure testing. In order to enable water to be removed following the hydrostatic pressure testing, internal water draining passageways 41 are provided in the areas of juncture between the generally vertically oriented hollow structural member 27 and the horizontally extending hollow structural member 31, as best seen in FIGS. 4 and 5 of the drawings. A water draining passageway 41 is located on each side of bulkhead 9 which extends substantially upwardly throughout the entire extent of the horizontally extending hollow structural member 31, and at least partially through the vertically extending hollow structural member 27 thereby to permit water to drain from curvilinear member 23 and vertical structural member 27 into the lower positioned horizontally extending hollow structural member 31.

At opposite ends of the horizontally extending hollow structure member 31, in the area of juncture with the channel-shaped member 23, at least along the lowermost extent thereof, internal water draining passageways 43 are provided in order to allow water to flow from the horizontally extending hollow structural member 31 into that portion of the channel-shaped member 23 which is positioned therebelow, as shown in FIG. 3. Water is thus able to drain from the channel-shaped member 23 through a water drain opening DO provided in the elongated shell 5, adjacent the lower juncture with the channel-shaped member 23.

Thus, gravity flow evacuation of water from within the interconnected hollow structural member assembly 21 is made possible by the water draining passageways 41 between the vertically oriented and horizontally extending hollow structural members 27, 31, respectively, and the water draining passageways 43 at the opposite ends of horizontally extending member 31 in the area of juncture with the channel-shaped member 23. From there, the water is drained out of the interconnected hollow structural member assembly 21 through the water drain opening DO in the elongated shell 5. Drain opening DO is preferably a threaded opening 45 in shell 5 in communication with the lowermost reaches of channel opening 25 of channel 23. A drain plug 47 is threaded into water drain opening 45 to seal off the aforesaid openings and passageways after entrapped water is drained therefrom so as to ensure that shell 5 is leak free.

The hydrostatic pressure testing method of the present invention, as herein described, permits filling the elongated shell 5 with water and pressurized to a predetermined pressure level (e.g., 22.5 PSI) so as to verify the structural integrity of the car, and then enables gravity flow evacuation of water from the elongated shell 5 including any water that may have entered the interconnected hollow structural assembly 23 or the like. Following removal of the water, the water drain openings 45 in the elongated shell 5 may be sealed off by the insertion of plugs 47 to prevent leakage from the car during internal pressurization.

By removing all or substantially all of the water from the interconnected hollow structural member assembly 21, entrappment of substantial quantities of water within the hollow members is eliminated (or substaintially reduced), and substantial savings in both time and materials to repair and/or rework the inside surfaces of the elongated shell 5 are realized.

As heretofore noted, the hollow members of assembly 21 may not be water tight. It is, however, preferred that such hollow members be water tight or seal so that lading particles or the like are prevented from accumulating therein inasmuch as these accumulated particles may lead to contamination of a lading or require expensive cleaning procedures. In accordance with this invention, if upon removing plugs 47 after hydrostatic testing water is found in assembly 21, air under pressure may be introduced into hollow assembly 21 via opening 45 and a bubble solution may be applied to the welds and joints of assembly 21 so as to aid in locating any air leak and to permit the ready sealing of such leaks, as by welding them closed.

In view of the above, it will be seen that the several objects of the invention are achieved, and other advantageous results are obtained.

As various changes could be made in the above constructions and methods without departing from the scope of the invention, it is intended that all matter contained the above description are shown in the accompanying drawings shall be interpreted as illustrative and not in a limiting sense.

I claim:

1. A railroad car comprising:
   a shell defining at least one internal compartment;
   interconnected hollow structural members within said shell with at least one of said hollow structural members being positioned at least partially below another of said hollow structural members, said shell being subjected to hydrostatic pressurization which may tend to at least partially fill said hollow structural members with water;
   an internal water draining passageway provided in said aforementioned hollow structural members in an area of juncture between said members; and
   a water drain opening in the lowermost region of said lowermost hollow structural member in communication with and cooperating with the water draining passageway thereby to facilitate the gravity flow of said water through said hollow structural members and evacuation therefrom.

2. The railroad car as defined in claim 1 having a plurality of said hollow structural members which are positioned at least partially below an adjacent hollow structural member, and a water draining passageway being provided in each area of juncture between of each of said hollow structural members.

3. The railroad car as defined in claim 2 wherein said water draining passageways are provided at least along a lowermost extent of each of said interconnected hollow structural members.

4. A railroad car comprising:
   a shell;
   a plurality of interconnected hollow structural members within said shell with at least certain of said hollow structural members being positioned at least partially below at least one of said hollow structural members;
   one or more internal water draining passageways provided in said aforementioned hollow structural members in areas of juncture between said members, said water draining passageways being provided at least along a lower most extent of each of interconnected hollow structural members;
   a water drain opening in the lower most region of said lower most hollow structural member in communication with and cooperating with the draining passageway thereby to facilitate the gravity flow of said water through said hollow structural members and the evacuation of said water therefrom; and
   said shell having a plurality of transverse bulkheads within said shell defining a plurality of compartments within said shell separated by said bulkheads, said interconnected hollow structural members being secured to said bulkhead adjacent the upper region thereof proximate the upper region of said shell.

5. The railroad car as defined in claim 4 wherein said interconnected hollow structural members include at least one generally vertically extending hollow member, at least one generally horizontally extending hollow member, and a generally curvilinearly extending hollow member.

6. The railroad car as defined in claim 5 wherein said generally curvilinear channel-shaped member has its channel opening facing said shell, said vertically oriented hollow structural member having its upper end connected to said channel-shaped member and with the channel opening of said channel-shaped member being in communication with the interior of said generally vertically oriented hollow structural member, said generally vertically oriented hollow structural member being attached at its lower end to one of said generally horizontally extending hollow structural member and having one of said internal water draining passageways in the area of juncture therebetween to permit communication with the interiors of said generally vertically oriented and horizontally extending hollow structural members, said generally horizontally extending hollow structural member also being connected to said curvilinear channel-shaped member at a position spaced from the connection of said generally vertically oriented hollow structural member therewith, another of said internal water draining passageways in the area of juncture of the generally horizontally extending hollow structural member with said curvilinear channel-shaped member, said water drain opening being in communication with the lowermost portion of said curvilinear channel-shaped member.

7. The railroad car as defined in claim 6 wherein the curvilinear channel-shaped member extends in substantially equal amounts on both sides of a vertical centerline extending through said elongated shell, said generally vertically oriented hollow structural members being provided on both sides of the vertical centerline of said shell, being connected at upper ends thereof to said curvilinear channel-shaped member, and being connected at lower ends to said generally horizontally extending hollow structural member with opposite ends of said generally horizontally extending hollow structural member being connected to said curvilinear channel-shaped member at positions spaced from the connections of said channel-shaped member with said generally vertically oriented hollow structural members.

8. The railroad car as defined in claim 1 further comprising a drain plug sealably inserted in said water drain opening when draining is complete.

9. In a railroad car having a shell defining at least one internal compartment and interconnected hollow structural members extending within said shell, at least one hollow structural member being positioned at least partially below another hollow structural member, the improvement comprising: a water draining passageway provided in said aforementioned hollow structural members in an area of juncture between said members, and a water drain opening in communication with and cooperating with the water draining passageway of said aforementioned hollow structural members in order to facilitate gravity flow of water through said hollow structural members and evacuation out of said elongated shell.

10. The improvement as defined in claim 9 and including a plurality of hollow structural members which are positioned at least partially below an adjacent hollow structural member and a water draining passageway being provided in the area of juncture of each of said interconnected hollow structural members, at least along a lowermost extent of said members.

* * * * *